United States Patent

Yamamoto et al.

[11] 3,988,067
[45] Oct. 26, 1976

[54] AUTOMATIC POLARIZATION ANALYZING DEVICE

[75] Inventors: Tadaaki Yamamoto, Tokyo; Toshiyuki Kasai; Yoshihiro Kaizawa, both of Kawasaki; Sakuji Watanabe, Urawa, all of Japan

[73] Assignee: Nippon Kogaku K.K., Tokyo, Japan

[22] Filed: Feb. 4, 1975

[21] Appl. No.: 546,903

Related U.S. Application Data

[63] Continuation-in-part of Ser. No. 425,811, Dec. 18, 1973, abandoned.

[30] Foreign Application Priority Data
Dec. 22, 1972 Japan............................ 47-128245

[52] U.S. Cl............................. 356/117; 324/99 R
[51] Int. Cl.²........................................ G01N 21/40
[58] Field of Search.............. 356/114, 116, 117; 324/99 R

[56] References Cited
UNITED STATES PATENTS

| | | | |
|---|---|---|---|
| 2,497,961 | 2/1950 | Shaw.................. | 324/99 D |
| 3,383,594 | 5/1968 | Fiorletta et al. ............. | 324/121 R |
| 3,687,555 | 8/1972 | Yamamoto et al. ............. | 356/114 |
| 3,714,569 | 1/1973 | Bruning et al. ................. | 324/99 D |
| 3,741,661 | 6/1973 | Yamamoto et al. ............. | 356/117 |
| 3,833,302 | 9/1974 | Hock ........................... | 356/114 |

*Primary Examiner*—John K. Corbin
*Assistant Examiner*—Richard A. Rosenberger
*Attorney, Agent, or Firm*—Fitzpatrick, Cella, Harper & Scinto

[57] ABSTRACT

In an automatic polarization analyzing device which employs the extinction detecting method using a light amplitude modulating system, two sets of converter means are provided for converting into an angle a positional deviation electrical signal corresponding to a dead zone present in the control system.

4 Claims, 7 Drawing Figures

AUTOMATIC POLARIZATION ANALYSING DEVICE

CROSS-REFERENCES TO RELATED APPLICATIONS

This is a continuation-in-part of copending application Ser. No. 425,811, filed Dec. 18, 1973, for AUTOMATIC POLARIZATION ANALYSING DEVICE, now abandoned.

BACKGROUND OF THE INVENTION

1. Field of the Invention

This invention relates to an automatic polarization analysing device, and more particularly to such a device in which positional deviation resulting from the presence of dead zones has been corrected.

2. Description of the Prior Art

It is usually the case with an automatic control device that an increase in its control sensitivity results in oscillations of a control system such as motors, gears and the like.

To prevent this, dead zones which are not responsive to the automatic control operation have heretofore been introduced into such systems. Likewise, in an automatic polarization analysing device (ellipsometer), the presence of such dead zones results in the production of positional deviations which, in turn, have led to failure to provide high accuracy in indications of azimuth and phase angles.

SUMMARY OF THE INVENTION

In view of the above-noted situations, we contribute by the present invention an automatic polarization analysing device in which a remaining electrical signal, or error voltage, corresponding to the positional deviation resulting from the presence of a dead zone during automatic control, may be converted into an angle the value of which may be added to an angle indication value detected by the automatic control. The accuracy of the angle is thereby enhanced and the dead zone may be increased as desired without reducing the accuracy of the angle indication, thereby increasing the service life of the control system.

The present invention contemplates the provision of an automatic polarization analysing device which comprises a polarization analysing optical system and two light modulators disposed therein for simultaneously modulating two polarization variables by two different AC voltage signals, the polarization variables determining the polarized state of a sample. Light receiving means is provided for photo-electrically converting the emergent light from the polarization analysing optical system, and two synchronous rectifier circuits are provided to which are applied signals in phase with respect to respective ones of the two AC voltage signals. The output signal from the light receiving means is also applied to each of these two rectifiers, thereby allowing the two combined modulated signals to be separately rectified. Two servo-motors are arranged to receive the outputs from respective ones of the synchronous rectifier circuits to rotate two elements in the polarization analysing optical system so that their angles of rotation correspond to the two polarization variables.

As a feature of the present invention, we provide two sets of converter means for converting into an angle the positional deviation electrical signal corresponding to a dead zone resulting from the servo-motors. Such two sets of converter means use as their inputs the outputs from respective ones of the two synchronous rectifier circuits.

A further feature of the present invention resides in the provision of means for indicating the two polarization variables of the sample corresponding to the amounts of rotation of the two elements in the polarization analysing optical system, and two sets of means for indicating the values provided by the two sets of converter means.

In another form of the present invention, the two light modulators use as their inputs respective ones of two composite AC voltage signals which comprise respective ones of the two AC voltage signals and respective higher harmonics. A filter circuit is disposed between each of the two synchronous rectifier circuits and each of the servo-motors to interrupt only the higher harmonic component. The converter means comprises two second synchronous rectifier circuits for synchronously rectifying the output signals from respective ones of the synchronous rectifier circuts by the frequencies of the higher harmonic components, and angle indicator circuits using as their inputs the outputs from respective ones of the second synchronous rectifier circuits and the outputs from respective ones of the filter circuits.

In yet another form of the present invention, the converter means comprises only one second synchronous rectifier circuit for synchronously rectifying the output signal from only one of the first synchronous rectifier circuits by the frequencies of the higher harmonic components, and angle indicator circuits using as their inputs the output from the second synchronous rectifier circuit and the outputs from respective ones of the first synchronous rectifier circuits.

There has thus been outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended hereto. Those skilled in the art will appreciate that the conception upon which this disclosure is based may readily be utilized as a basis for the designing of other structures for carrying out the several purposes of the invention. It is important, therefore, that the claims be regarded as including such equivalent constructions as do not depart from the spirit and scope of the invention.

BRIEF DESCRIPTION OF THE DRAWINGS

Specific embodiments of the invention have been chosen for purposes of illustration and description, and are shown in the accompanying drawings, forming a part of the specification wherein.

DESCRIPTION OF THE PREFERRED EMBODIMENTS

Figure 1:
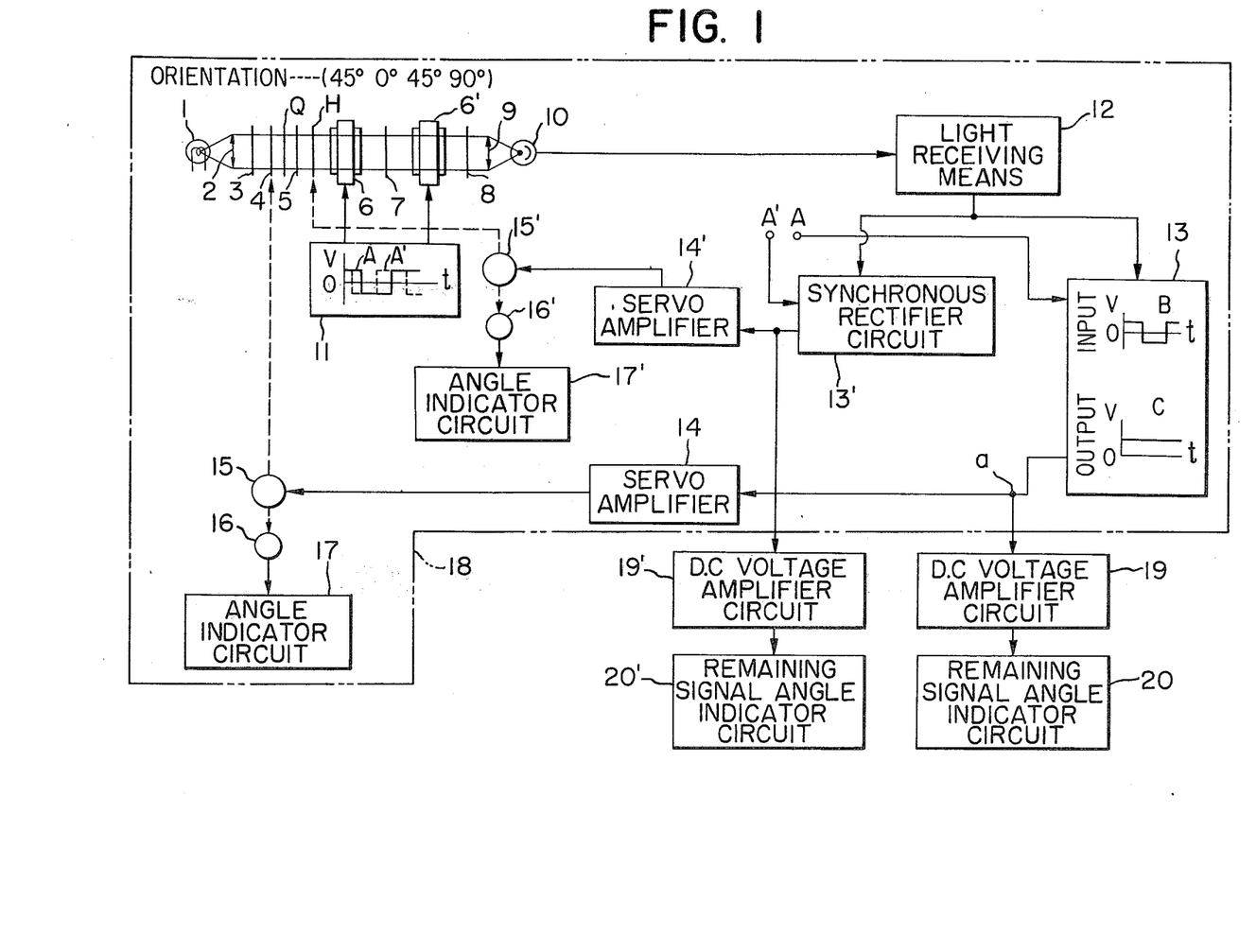
FIG. 1 is a block diagram of the automatic polarization analysing device according to an embodiment of the present invention.

Referring to FIG. 1, there is diagrammatically shown an embodiment of the present invention which includes a light source 1, a collimator lens system 2, a monochrome filter 3 (usually of 546 mu), and a polarizer 4 rotatable about the optical axis and operatively associated with a servo-motor 15, which will later be described. Letter Q designates a ¼ wavelength plate whose azimuth is set to 45°. There is further seen a sample 5 which is set to any desired azimuth, a ½ wavelength plate H operatively associated with a servo-motor 15' which will also later be described, and a light modulator 6 such as K.D.P. whose major axis azimuth is maintained at 45° and to which a light modulator element drive circuit 11 applies an AC voltage of frequency $f$ (square wave A). There is further provided a similar light modulator 6' whose major axis azimuth is maintained at 45° and to which the light modulator element drive circuit 11 applies a square wave A' of frequency $f$ but 90° out of phase with respect to the aforesaid square wave A. Numeral 7 designates a ¼ wavelength plate whose major axis azimuth is maintained at 0° and which converts the phase modulation effected by said light modulator 6 into an azimuth modulation. Further provided is an analyser 8 whose azimuth is fixed at 90°, a condenser lens system 9, a light receiving means 10 such as a photocell or the like, a light receiving circuit 12, a synchronous rectifier circuit 13 for deriving, out of the photoelectric current from the light receiving means 12, a signal component of frequency $f$ in phase with respect to the signal A from the light modulator element drive circuit 11 and for rectifying such signal component, and a synchronous rectifier circuit 13' for deriving, out of the photoelectric current from the light receiving circuit 12, a signal component of frequency $f$ in phase with respect to the signal A' from the light modulator element drive circuit 11 and for rectifying such signal component. A servo-amplifier 14 is provided to amplify the output from the synchronous rectifier circuit 13 and to apply such amplified output signal to a servo-motor 15. A potentiometer 16 is operatively associated with the servo-motor 15 to produce a signal representing the amount of rotation of the polarizer 4. Numeral 17 denotes an angle indicator circuit for indicating the azimuth angle by means of the signal from the potentiometer 16. Likewise, a servo-amplifier 14' is provided to amplify the output signal from the synchronous rectifier circuit 13' and to apply such amplified output signal to a servo-motor 15'. A potentiometer 16' is operatively associated with the servo-motor 15' to produce a signal representing the amount of rotation of the ½ wavelength plate H, and numeral 17' denotes an angle indicator circuit for receiving the signal from the potentiometer and thereby indicating the phase angle.

The above-described parts 1–17, 13'–17', Q and H, together constitute a conventional polarization analysing device 18 for automatically measuring two polarization variables possessed by a sample. Also, the parts 1–5, 7–9, Q and H, constitute a polarization analysing optical system.

Description will now be made of the automatic control operation effected by such automatic polarization analysing device 18. For simplicity, an embodiment of the present invention will be described with respect to the detection of one of the two polarization variables, i.e., the azimuth angle, because it is believed that detection of the other polarization variable can be effected entirely in the same manner as will be described hereinafter.

Figure 2:
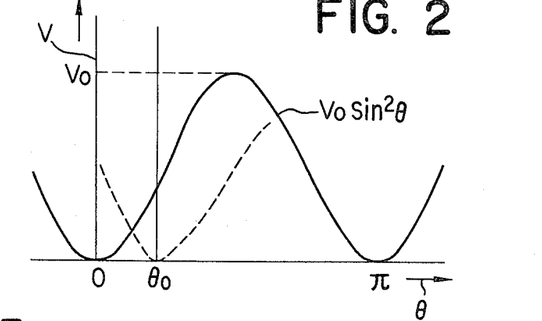
FIGS. 2, 3 and 4 illustrate the operating waveforms in the embodiment of FIG. 1.

Initially, with the sample 5 being kept aside from the polarization analysing optical system and with the AC voltage waveform (square wave A) being still left unapplied, the relation between the angle of rotation of the polarizer and the output signal from the light receiving circuit may be represented by a waveform $V_0 \sin^2\theta$ as shown in the graph of FIG. 2. In this graph, the ordinate represents a voltage V proportional to the quantity of light while the abscissa represents the angle of rotation $\theta$ of the polarizer 4. The peak voltage value (amplitude) is indicated by $V_0$. Here, it is assumed that the position of the polarizer 4, when the quantity of light received by the light receiving means 10 is maximum with the sample kept aside from the polarization analysing optical system, is set to zero (0); and under such conditions, an AC voltage wavefrom (square wave A) is applied from the light modulator element drive circuit to the light modulator 6, whereafter the polarizer 4 is rotated from the zero position to a desired angle $\theta_0$. The following description is based on this assumption. The light receiving circuit 12 produces a voltage waveform (square wave B) corresponding to the received light, which waveform provides an output signal to the synchronous rectifier circuit 13.

Figure 3:
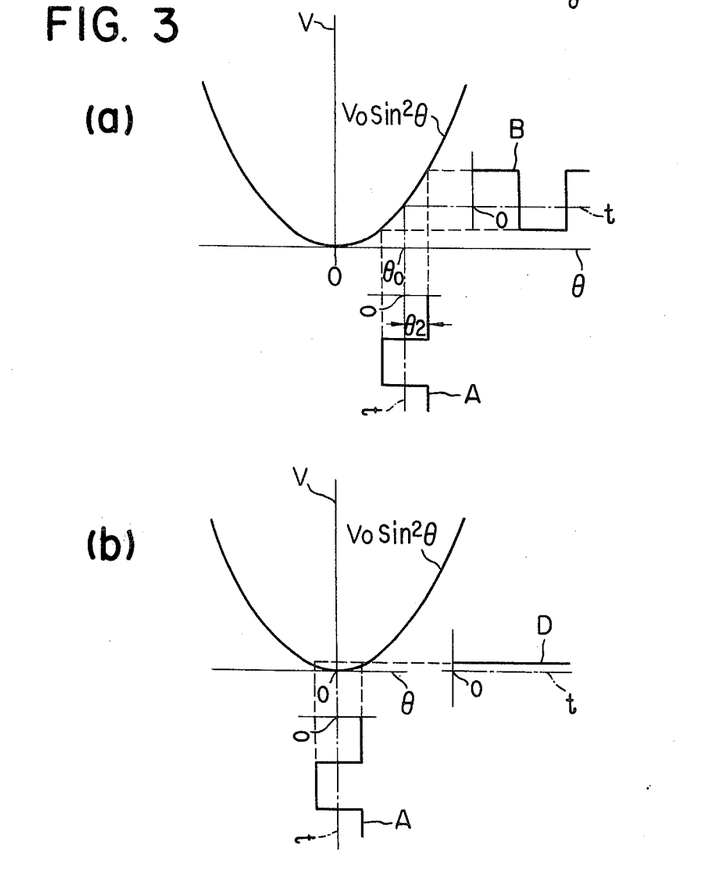

This output signal (square wave B) is then rectified by the synchronous rectifier circuit 13 into a DC wave C, which provides an output signal to the servo-amplifier 14 (see FIG. 1), whose output signal in turn energizes the servo-motor 15. In response thereto, the polarizer 4 is also rotated and continues the rotation until the voltage waveform produced by the light receiving circuit 12 assumes a DC wave D as shown in FIG. 3(b), whereupon the output from the synchronous rectifier circuit 13 becomes null to deenergize the servo-motor 15, thus completing an automatic control operation.

Thus, the polarizer 4 is rotated only by an angle of $\theta_0$ from the angular position $\theta_0$ to the initial position O, and such angular position $\theta_0$ of the polarizer is indicated by the angle indicator circuit 17.

With a sample of azimuth angle $\theta_0$ inserted in the measuring optical system, the relation between the angle of rotation of the polarizer and the output of the light receiving circuit is such as shown by the dotted curve in FIG. 2, which curve is the curve of $V_0 \sin^2\theta$ horizontally displaced along the abscissa by an amount $\theta_0$ indicating that the polarizer is only rotated by an angle of $\theta_0$, whereafter the automatic control operation ceases and the value then indicated by the angle indicator circuit is the azimuth angle $\theta_0$ of the sample.

Figure 4:
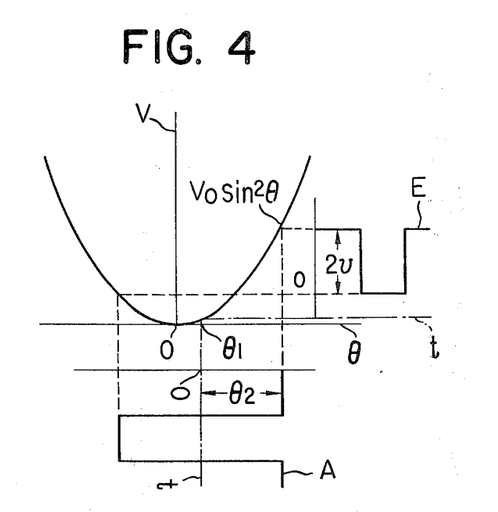

For the above-described reasons, however, such an automatic control system is not capable of completely returning the polarizer to its initial position (the position O) and thus, the exact value of the azimuth angle $\theta_0$ may not be indicated when the sample is inserted in place. In fact, there is produced a positional deviation $\theta_1$ as shown in FIG. 4, and this causes an electrical signal representative of such deviation in the form of square wave E to remain in the light receiving circuit 12. Therefore, the remaining signal (the positional deviation signal) $v^*$ at the output terminal point $a$ of the synchronous rectifier circuit 13 may be expressed as:

$$v^* = V_0/2 \{\sin^2(\theta_2+\theta_1) - \sin^2(\theta_2-\theta_1)\} = V_0/2 \sin 2\theta_2 \cdot \sin 2\theta_1 \approx (V_0 \sin 2\theta_2)\theta_1 \quad \ldots \quad (1),$$

where $\theta_1 << \theta_2$ and $\theta_2$ is the amplitude of the light modulation input (square wave A) from the light modulator element drive circuit 11.

A DC voltage amplifier circuit 19 is connected to the output terminal point $a$ of the synchronous rectifier circuit 13 to amplify the remaining signal voltage $v^*$, which is applied to a remaining signal angle indicator circuit 20 for conversion into an angle, designed so as to satisfy the following relation given by the aforesaid formula (1):

$$\theta \approx \frac{v^*}{V_0 \sin 2\theta_2}$$

Thus, by summing up the azimuth angle as detected by the remaining signal angle indicator circuit 20 and the azimuth angle as detected by the aforesaid angle indicator circuit 17, an azimuth angle having the positional deviation $\theta_1$ corrected may be detected. Alternatively, the angle indicator circuit 17 may be arranged so as to indicate the azimuth angle having the positional deviation $\theta_1$ corrected.

As to the measurement of the phase difference which has not been described hitherto, it may be understood by replacing the parts 6, 13, 14, 15, 16, 17, 19 and 20 with functionally similar substitutes such as light modulator 6', synchronous rectifier circuit 13', servo-amplifier 14', servo-motor 15' operatively associated with ½ wavelength plate H, potentiometer 16', angle indicator circuit 17', DC voltage amplifier circuit 19' and remaining signal angle indicator circuit 20'. In this case, however, it should be noted that the AC voltages (square waves A and A') applied to the light modulators 6 and 6', and necessarily the control signals A and A' applied to the synchronous rectifier circuits 13 and 13', are 90° out of phase with respect to each other in order to divide the photoelectric current from the light receiving circuit 12 into two currents for the synchronous rectifier circuits 13 and 13'.

In the present embodiment, the two AC voltage signals applied to the light modulators have been described as square waves which are 90° out of phase, whereas, the same result as described may be obtained by using two square waves of different frequencies. In this latter case, it will be apparent that the signals applied to the two synchronous rectifier circuits 13 and 13' must be either two AC voltage signals of different frequencies or two signals identical in phase thereto (such as sine waves).

In the foregoing embodiments, deterioration of the light source, absorption of the light by the sample, variation in the reflection factor during the polarization analysis by reflection, etc., may result in a variation in the peak voltage value (amplitude) $V_0$ in the light receiving circuit 12, that is, a variation in the quantity of incident light, and such variation in $V_0$ must be automatically compensated for because it makes it impossible to provide any accurate azimuth indication. Another embodiment of the present invention which incorporates means for such compensation will now be described.

Figure 5:
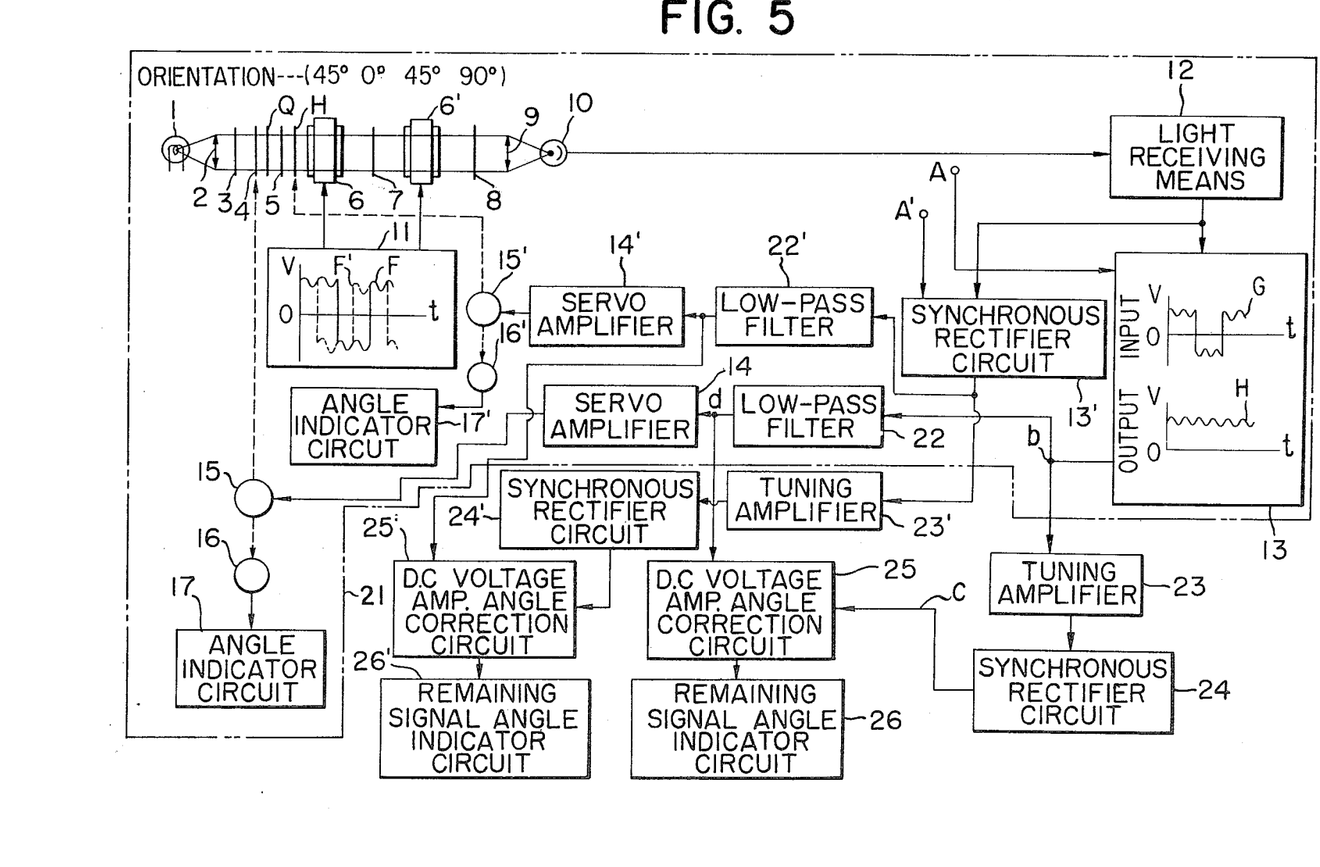
FIG. 5 is a block diagram of the automatic polarization analysing device according to another embodiment of the present invention.
Figure 6:
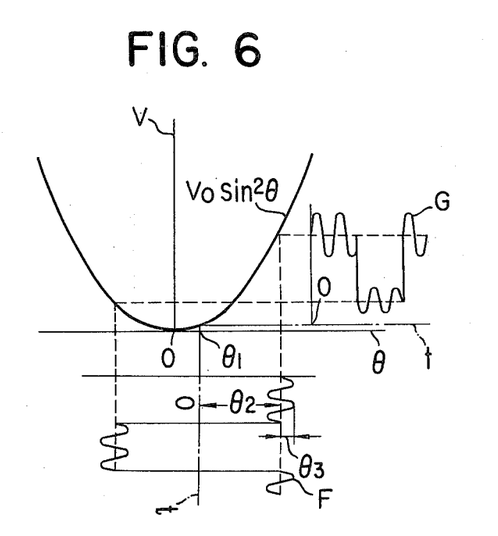
FIG. 6 illustrates the operating waveforms in the embodiment of FIG. 5.

Referring to FIG. 5, an automatic polarization analysing device is generally designated by numeral 21 and differs in the following points from that designated by numeral 18 in FIG. 1. AC voltages A and A' of frequency $f$ plus an automatic amplitude compensation signal of frequency $f_0$ ($f<<f_0$) are applied to the light modulator element drive circuit 11, so that a composite AC voltage (composite wave F), comprising the signal A and the signal of frequency $f_0$, is applied to the light modulator 6. A composition AC voltage signal (composite wave F') comprising the signal A' and the signal of frequency $f_0$ are applied to the light modulator 6'. The light receiving circuit 12 produces a modulated voltage waveform (composite wave G) as shown in FIG. 6, which provides an output signal to the synchronous rectifier circuits 13 and 13'. On the other hand, these synchronous rectifier circuits respectively receive, as their inputs, square waves A and A' as in embodiment of FIG. 1. Description will particularly be made only of the detection of the azimuth angle. Only a signal component of frequency $f$ of the output signal (composite signal G) is rectified by the synchronous rectifier circuit 13 to provide an output signal H having a component frequency $f_0$ as shown in FIG. 5. Numeral 22 designages a low-pass filter circuit for interrupting the frequency $f_0$ component of the output signal H.

A tuning amplifier 23 for center frequency $f_0$ is connected to the output terminal point $b$ of the synchronous rectifier circuit 13, and a synchronous rectifier circuit 24 for center frequency $f_0$ is connected to the tuning amplifier 23. By these means, the automatic amplitude compensation signal is detected and rectified to provide an output signal to a DC voltage amplification angle correction circuit 25, which in turn is connected to the output terminal $d$ of the low-pass filter circuit 22. Numeral 26 designates a remaining signal angle indicator circuit.

The principle of automatic compensation for the variation in $V_0$ will now be described. The output voltage $E_1$ at the output terminal point $c$ of the synchronous rectifier circuit 24 for any given quantity of incident light $V_1$ is expressed as:

$$E_1 = \tfrac{1}{2} \cdot V_1/2 \{\sin^2(\theta_2 + \theta_1 + \theta_3) - \sin^2(\theta_2+\theta_1-\theta_3) + \sin^2(\theta_2-\theta_1+\theta_3) - \sin^2(\theta_2 - \theta_1 + \theta_3)\} \cdot 2/\pi = V_1/2\pi \cdot 2\sin 2\theta_2 \cdot \sin 2\theta_3 \cdot \cos 2\theta_1 \approx V_1/\pi \sin 2\theta_2 \cdot \sin 2\theta_3 \quad \ldots \quad (2),$$

where $|\theta_1| << |\theta_2| - |\theta_3|$, $\theta_3$ is the amplitude of the automatic amplitude compensation signal (of frequency $f_0$), and $V_1$ is a voltage proportional to the quantity of incident light (i.e., the variable voltage to be compensated for). On the other hand, the output voltage $v1$ at the output terminal point $d$ of the low-pass filter circuit 22 is given by formula (1):

$$v^*1 \approx (V_1 \sin 2\theta_2) \theta_1 \quad \ldots \quad (3),$$

As a result, $V_1$ can be eliminated by formulae (2) and (3), thus giving:

$$\theta_1 \approx \frac{\sin 2\theta_3}{\pi} \frac{v^*1}{E_1} \quad (4)$$

Hence, by designing the DC voltage amplification angle correction circuit 25 using the two output voltage $v^*1$ and $E_1$ as inputs and the remaining signal angle indicator circuit 26 so as to satisfy the relation (4) above, it is possible to detect the remaining azimuth angle in which $V_1$, i.e., the variation in $V_0$, has been automatically compensated for. Thus, the present embodiment can detect the azimuth angle in which not only the positional deviation $\theta_1$ has been corrected as in the embodiment of FIG. 1, but also any error resulting from the variation in the quantity of incident light caused by the various factors previously mentioned has been corrected.

Figure 7:
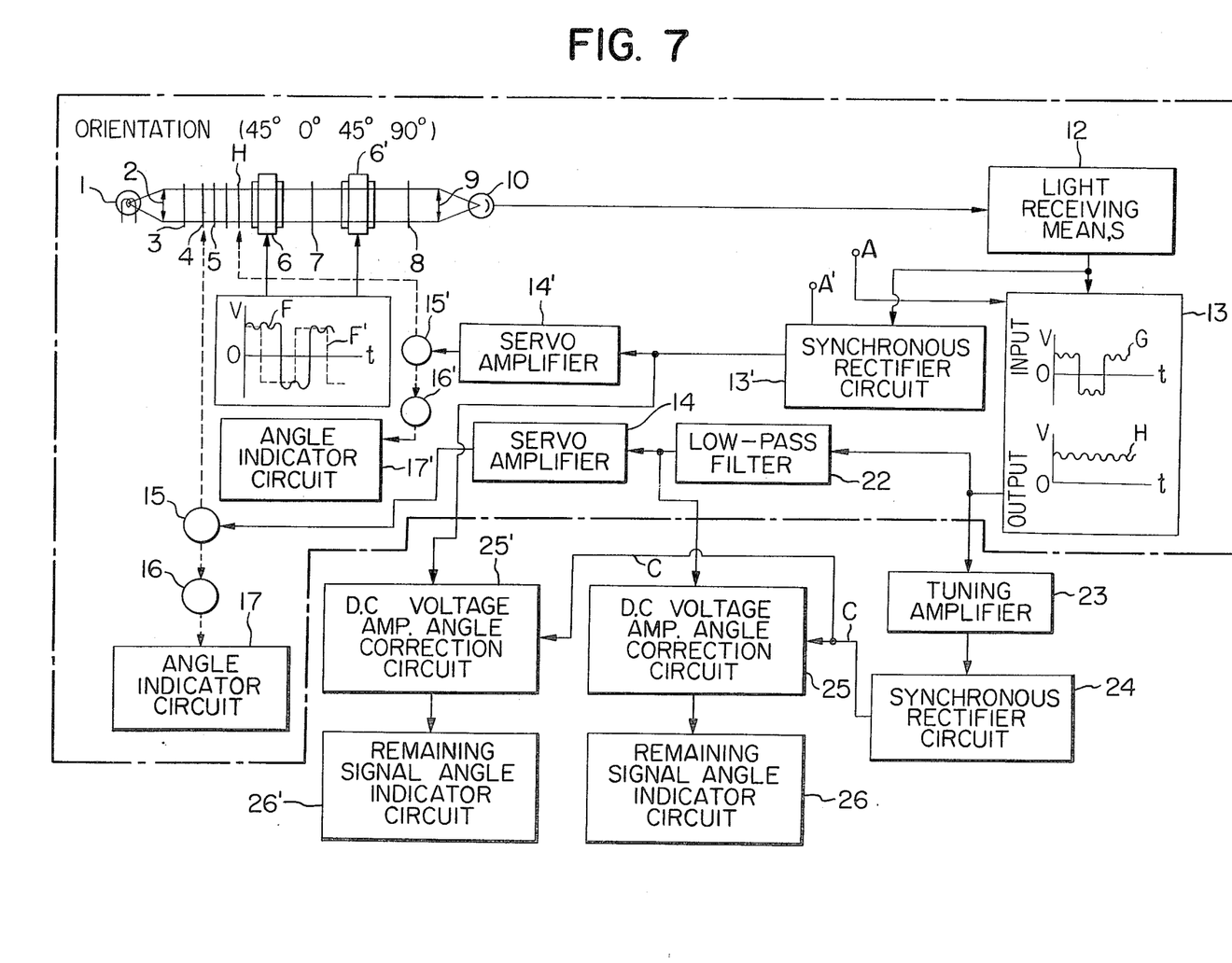
FIG. 7 is a block diagram of the automatic polarization analysing device according to yet another embodiment of the present invention.

In the embodiment shown in FIG. 5 of the present application, an amplitude compensating signal of frequency $f_0$ is added to both square wave voltages A and A' of frequency $f$, and an amplitude compensation signal is thereby obtained. FIG. 7 shows yet another embodiment of the present invention wherein the compensating signal $f_0$ is added only to the modulating square wave A. The other modulating square wave A' remains uncompensated. It has been found that by properly arranging the elements of the system certain elements can be eliminated without any loss in accuracy of indication. In the arrangement of FIG. 7 the amplitude correction signal obtained from one of the second synchronous rectifier circuits is applied to the inputs of each of the correction circuits 25 and 25'. Thus, as shown in FIG. 7, the output of the rectifier circuit 24 is connected in common to the correction circuits 25 and 25'. Only the waveform A must now carry the compensation signal of frequency $f_0$. The waveform A' may have the shape of a simple square wave, as in FIG. 1. It will be appreciated that in the embodiment of FIG. 7, there is no need for a second low-pass filter, since in that embodiment no high frequency component on the signal emanates from the first synchronous rectifier circuit 13'. In addition, in the embodiment of FIG. 7, there is no tuning amplifier and no second synchronous rectifier circuit. Nevertheless, it will be appreciated that it is possible to achieve a satisfactory overall compensating effect with a reduced number of components.

As to the measurement of the phase difference which has been omitted in the foregoing description, it may be understood by replacing the parts 6, 13, 14, 15, 16, 17, 22, 23, 24, 25 and 26 with functionally similar substitutes such as light modulator 6', synchronous rectifier circuit 13', servo-amplifier 14' servo-motor 15' operatively associated with ½ wavelength plate H, potentiometer 16', angle indicator circuit 17', low-pass filter 22', tuning amplifier 23', synchronous rectifier circuit 24', DC voltage amplication angle correction circuit 25' and remaining signal angle indicator circuit 26'. The signal applied to the light modulator 6' is necessarily a composite AC voltage comprising one of the signal components applied to the light modulator 6 which is 90° out of phase with respect to the other signal component of frequency $f$, and an automatic amplitude compensation signal of frequency $f_0$.

Thus, according to the present invention, the remaining electrical signal corresponding to the positional deviation $\theta_1$ resulting from the presence of the dead zone can be converted into an angle and the resultant value may be added to angle indication value detected by the automatic control, whereby the accuracy of the angle indication may be enhanced and in addition, the dead zone may be increased as desired, without the accuracy of the angle indication being reduced. This in turn contributes to a greatly increased service life of the control system as compared with the conventional devices of this type.

Further, the present invention can correct the measurement error resulting from the various factors such as deterioration of the light source, absorption of the light by the sample, variation in the reflection factor during the polarization analysis by reflection, etc., thus further improving the accuracy of the angle indication.

We believe that the construction and operation of our novel automatic polarization analysing device will now be understood, and that the advantages thereof will be fully appreciated by those persons skilled in the art.

We claim:
1. An automatic polarization analysing device comprising a polarization analysing optical system including at least a light source and first and second light modulators for simultaneously modulating a beam of light by two different AC square wave signals such that one of said AC square wave signals is a composite of a basic signal frequency ($f$) plus an automatic amplitude compensation signal frequency (fo) which is higher than the basic signal frequency (fo>$f$), the polarization analysing optical system being operable to generate two light signals modulated by said two light modulators which signals correspond respectively to two polarization variables of a sample,
   a photoelectric conversion means for converting said two light signals to two electric signals,
   a first synchronous rectifier circuit for deriving and rectifying one of said two electric signals,
   a second synchronous rectifier circuit for deriving and rectifying the other of said two electric signals,
   a first servo motor arranged to rotate one element of said optical system in accordance with the signal from said first synchronous rectifier circuit,
   a second servo motor arranged to rotate the other element of said optical system in accordance with the signal from said second synchronous rectifier circuit,
   a first and second means for indicating the angles of rotation of said elements,
   a low-pass filter connected to receive the signal from said first synchronous rectifier circuit and to interrupt the higher frequency signal component (fo), said filter also being connected to provide driving control signals to said first servo motor,
   a first operation circuit for converting a remaining error voltage between the low-pass filter and the first servo motor, due to a dead zone thereof, to an output value corresponding to the difference between the actual angle of rotation of said one element by said first servo motor and that angle of rotation of said one element which would have been obtained in the absence of said dead zone,
   a second operation circuit for converting a remaining error voltage between said second synchronous rectifier circuit and the second servo motor, due to a dead zone thereof, to an output value corresponding to the difference between the actual angle of rotation of said other element by said servo mtor and that angle of rotation of said other element which would have been obtained in the absence of said dead zone,
   amplitude compensating signal detecting means connected to receive the signal from said first synchronous rectifier circuit, and to derive and rectify only the higher frequency signal component (fo) to generate an amplitude correction signal which corresponds to the variation in the emergent light quantity from said polarization analyzing optical system which variation is caused by deterioration of said light source or the like, said compensating signal detecting means being connected to transmit said amplitude correction signal to both said first and second operation circuits;

a third indicating means for indicating an output value from said first operation circuit, and a fourth indicating means for indicating an output value from said second operation circuit, whereby said first and second operation circuits receive said amplitude correction signal and said remaining error voltages, respectively, and convert them to said output values which correspond to angles of rotation through which said two elements have not been rotated in correspondence with the emergent light quantity from the polarization analysing optical system, said third and fourth indicating means indicating said angles, respectively.

2. An automatic polarization analysing device comprising a polarization analysing optical system including at least a light source and first and second light modulators for simultaneously modulating a beam of light by two different AC square wave signals such that said AC square wave signals are each a composite of a basic signal frequency ($f$) plus an automatic amplitude compensation signal frequency ($fo$) which is then the basic signal frequency ($fo>f$), the polarization analysing optical system being operable to generate two light signals modulated by said two light modulators which signals correspond respectively to two polarization variables of a sample, a photoelectric conversion means for converting said two light signals to two electric signals, a first synchronous rectifier circuit for deriving and rectifying one of said two electric signals, a second synchronous rectifier circuit for deriving and rectifying the other of said two electric signals, a first servo motor arranged to rotate one element of said optical system in accordance with the signal from said first synchronous rectifier circuit, a second servo motor arranged to rotate the other element of said optical system in accordance with the signal from said second synchronous rectifier circuit, a first and second indicating means for indicating the angles of rotation of said two elements, a first low-pass filter connected to receive the signal from the first synchronous rectifier circuit and to interrupt the higher frequency signal component ($fo$) from said signal, said first low-pass filter also being connected to provide driving control signals to said first servo motor, a second low-pass filter connected to receive the signal from said second synchronous rectifier circuit and to interrupt said higher frequency signal component ($fo$) from said signal, said second low-pass filter also being connected to provide driving control signals to said second servo motor, a first operation circuit for converting a remaining error voltage between the first low-pass filter and the first servo motor, due to a dead zone thereof, to an output value corresponding to the difference between the actual angle of rotation of said one element by said first servo motor and that angle of rotation of said one element which would have been obtained in the absence of said dead zone, a second operation circuit for converting a remaining error voltage between the second low-pass filter and the second servo motor, due to a dead zone thereof, to an output value corresponding to the difference between the actual angle of rotation of said other element by said second servo motor and that angle of rotation of said other element which would have been obtained in the absence of said dead zone, first amplitude compensating signal detecting means connected to receive the signal from said first synchronous rectifier circuit, and to derive and rectify only said higher frequency signal component ($fo$) to generate a first amplitude correction signal which corresponds to the variation in the emergent light quantity from said polarization analysing optical system which variation is caused by deterioration of said light source or the like, said first compensating signal detecting means being connected to transmit said first amplitude correction signal to said first operation circuit, second amplitude compensating signal detecting means connected to receive the signal from said second synchronous rectifier circuit, thereby deriving and rectifying only said higher frequency signal component ($fo$) to generate a second amplitude correction signal which corresponds to said variation, said second compensating signal detecting means being connected to transmit said second amplitude correction signal to said second operation circuit, a third indicating means for indicating an output value of the first operation circuit, and a fourth indicating means for indicating an output value of the second operation circuit, whereby said first and second operation circuits receive said amplitude correction signals and said remaining error voltages, respectively, and convert them to said output values which correspond to angles of rotation through which said two elements have not been rotated in correspondence with the emergent light quantity from the polarization analysing optical system, said third and fourth indicating means indicating said angles, respectively.

3. An automatic polarization analysing device comprising a polarization analysing optical system including at least a light source and first and second light modulators for simultaneously modulating a beam of light by two different AC square wave signals such that at least one of said AC square wave signals is a composite of a basic signal frequency ($f$) plus an automatic amplitude compensation signal frequency ($fo$) which is higher than the basic signal frequency ($fo>f$), the polarization analysing optical system being operable to generate two light signals modulated by said two light modulators which signals correspond respectively to two polarization variables of a sample, a photoelectric conversion means for converting said two light signals to two corresponding electric signals, a first synchronous rectifier circuit for deriving and rectifying the electric signal corresponding to said one AC square wave signal, a second synchronous rectifier circuit for deriving and rectifying the other of said two electric signals, a first servo motor arranged to rotate one element of said optical system in accordance with the signal from said first synchronous rectifier circuit, a second servo motor arranged to rotate the other element of said optical system in accordance with the signal from said second synchronous rectifier circuit, a first and second means for indicating the angles of rotation of said two elements, a low-pass filter connected to receive the signal from said first synchronous rectifier circuit and to interrupt the higher frequency signal component (fo) from said signal, said filter also being connected to provide driving control signals to said first servo motor, a first operation circuit for converting a remaining error voltage between said low-pass filter and said first servo motor, due to a dead zone thereof, to an output value corresponding to the difference between the actual angle of rotation of said one element by said first servo motor and that angle of rotation of said one element which would have been obtained in the absence of said dead zone, a second operation circuit for converting a remaining error voltage between the second synchronous rectifier and the second servo motor, due to a dead zone thereof, to an output value corresponding to the difference between the actual angle of rotation of said other element by said second servo motor and that angle of rotation of said other element which would have been obtained in the absence of said dead zone, an amplitude compensating signal detecting means connected to receive the signal from said first synchronous rectifier circuit, and to derive and rectify only said higher frequency signal component (fo) to generate an amplitude correction signal which corresponds to the variation in the emergent light quantity from said polarization analysing optical system which variation is caused by deterioration of said light source or the like, said amplitude compensating signal detecting means being connected to transmit said correction signal to said first operation circuit, a third indicating means for indicating an output value of the first operation circuit, and a fourth indicating means for indicating an output value of the second operation circuit, whereby said first and second operation circuits receive said amplitude correction signal and said remaining error voltages, respectively, and convert them to said output values which correspond to angles of rotation through which said two elements have not been rotated in correspondence with the emergent light quantity from the polarization analysing optical system, said third and fourth indicating means indicating said angles, respectively.

4. An automatic polarization analysing device including a polarization analysing optical system comprising two light modulators disposed in said polarization analysing optical system for simultaneously modulating a beam of light by two different AC voltage signals, each of said modulations being operable to determine a polarization variable of a sample, said two light modulators having as their inputs respective ones of two composite AC voltage signals, said composite Ac voltage signals comprising respective ones of said two AC voltage signals and respective ones of two higher frequency components, light receiving means for photoelectrically converting the emergent light from said polarization analysing optical system, two first synchronous rectifier circuits connected to receive signals which are in phase with respect to respective ones of said two AC voltage signals, whereby each of said rectifier circuits rectifies only a respective one of said two AC voltage signals, two servo motors, each arranged to rotate a respective element of said optical system in accordance with the output signals from respective ones of said first synchronous rectifier circuits so that their angles of rotation correspond to said two polarization variables, each of said servo motors having an associated dead zone, two filter circuits, each of whch is disposed, respectively, between each of said two first synchronous rectifier circuits and each of said two servo motors to interrupt only said higher frequency component, two sets of converter means each connected to a respective output of one of said first synchronous rectifier circuits, each of said converter means being operable to produce a response corresponding to angular deviation electrical signals which appear, at said outputs, said deviation signals resulting from said dead zones, said two sets of converter means each comprising two second synchronous rectifier circuits, each one of which is operable to synchronously rectify output signals from respective ones of said first synchronous rectifier circuits, said output signals having said respective higher frequency components, and angle indicator circuits using as their inputs the outputs from respective ones of said second synchronous rectifier circuits and the outputs from respective ones of said filter circuits.

* * * * *

UNITED STATES PATENT AND TRADEMARK OFFICE
CERTIFICATE OF CORRECTION

PATENT NO. : 3,988,067
DATED : October 26, 1976
INVENTOR(S) : TADAAKI YAMAMOTO, et al.

It is certified that error appears in the above-identified patent and that said Letters Patent are hereby corrected as shown below:

Column 1, line 69, before "servo-motors" insert -- two --.
Column 6, line 19, after "in" insert -- the --; line 35, after "terminal" insert -- point --; line 45, change second line of equation to read -- $\sin^2(\theta_2-\theta_1+\theta_3)-\sin^2(\theta_2-\theta_1-\theta_3)\} \cdot 2/\pi = V_1/2\pi$ . --; line 53, change "v1" to -- v*1 --.
Column 7, line 61, before "angle" insert -- the --.
Column 8, line 60, change "mtor" to -- motor.
Column 9, line 28, change "then" to -- higher than --.

Signed and Sealed this

Twenty-second Day of February 1977

[SEAL]

Attest:

RUTH C. MASON
*Attesting Officer*

C. MARSHALL DANN
*Commissioner of Patents and Trademarks*